(12) United States Patent
Papp et al.

(10) Patent No.: US 7,321,068 B2
(45) Date of Patent: Jan. 22, 2008

(54) METHOD FOR PRODUCING TRICYCLODECANDIALDEHYDE

(75) Inventors: Rainer Papp, Speyer (DE); Rocco Paciello, Bad Dürkheim (DE); Christoph Benisch, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/581,802

(22) PCT Filed: Dec. 14, 2004

(86) PCT No.: PCT/EP2004/013814

§ 371 (c)(1),
(2), (4) Date: Jun. 5, 2006

(87) PCT Pub. No.: WO2005/058786

PCT Pub. Date: Jun. 30, 2005

(65) Prior Publication Data

US 2007/0100168 A1    May 3, 2007

(30) Foreign Application Priority Data

Dec. 9, 2003   (DE) ................ 103 57 718

(51) Int. Cl.
    *C07C 45/50*   (2006.01)
    *C07C 35/21*   (2006.01)
    *C07C 209/00*  (2006.01)

(52) U.S. Cl. ................. 568/444; 568/816; 564/446

(58) Field of Classification Search .............. None
See application file for complete search history.

(56) References Cited

U.S. PATENT DOCUMENTS

| | | | |
|---|---|---|---|
| 3,499,933 A | 3/1970 | Pruett et al. | |
| 3,716,626 A | 2/1973 | Kniese et al. | |
| 4,386,018 A | 5/1983 | Merger et al. | |
| 4,400,547 A | 8/1983 | Dawes et al. | |
| 4,517,391 A | 5/1985 | Schuster et al. | |
| 4,709,105 A | 11/1987 | Grenacher et al. | |
| 4,778,929 A | 10/1988 | Zehner et al. | |
| 5,037,793 A | 8/1991 | Toussaint et al. | |
| 5,041,675 A | 8/1991 | Lukas et al. | |
| 5,107,018 A | 4/1992 | Schuster | |
| 5,208,194 A | 5/1993 | Pitchai et al. | |
| 5,728,893 A | 3/1998 | Becker et al. | |
| 6,310,261 B1 | 10/2001 | Geissler et al. | |
| 6,765,119 B2 | 7/2004 | Hoffmann et al. | |
| 2002/0159930 A1 | 10/2002 | Zehner et al. | |

FOREIGN PATENT DOCUMENTS

| CA | 2025829 | 9/1989 |
|---|---|---|
| DE | 1954315 | 5/1971 |
| DE | 1618384 | 9/1971 |
| DE | 2321101 | 11/1974 |
| DE | 2519817 | 11/1976 |
| DE | 2628987 | 1/1978 |
| DE | 2366264 | 4/1980 |
| DE | 3904083 | 8/1990 |
| DE | 3932332 | 4/1991 |
| EP | 0026983 | 9/1980 |
| EP | 0044444 | 6/1981 |
| EP | 0100406 | 5/1983 |
| EP | 0147219 | 12/1984 |
| EP | 0224872 | 11/1986 |
| EP | 0285420 | 3/1988 |
| EP | 0348832 | 6/1989 |
| EP | 0394842 | 4/1990 |
| EP | 0415202 | 8/1990 |
| EP | 0423769 | 10/1990 |
| EP | 1065194 | 6/2000 |
| EP | 1231198 | 2/2002 |
| GB | 1170226 | 11/1969 |
| GB | 1450700 | 9/1976 |
| GB | 1551741 | 8/1979 |
| GB | 1579159 | 11/1980 |
| WO | WO-93/02024 | 2/1993 |
| WO | WO-99/36382 | 7/1999 |
| WO | WO-00/09467 | 2/2000 |
| WO | WO-02/20451 | 3/2000 |
| WO | WO-01/87809 | 11/2001 |

OTHER PUBLICATIONS

Cornils et al., "Derivate des Dicyclopentadiens-aktuelle Schlüsselverbindungen", Chemiker-Zeitung, vol. 98, No. 2, Jahrgang, 1974, pp. 70-76.
Pruett, "Industrial Organic Chemicals Through Utilization of Synthesis Gas", The New York Academy of Sciences, vol. 295, 1977, pp. 238-242.
Pruett, "Advances in Organometallic Chemistry", Academic Press, vol. 17, 1979, pp. 32-33 and 58-59.
Falbe, "New Syntheses with Carbon Monoxide", Springer-Verlag, 1980, pp. 38-45.
Falbe et al., "Synthesen mit Kohlenmonoxyd XI [1]) Zur Hydroformylierung des Bicycloheptenaldehyds und des Dicyclopentadiens", Brennstoff-Chemie, No. 6, vol. 48, 1967, pp. 182-184.
Houben-Weyl: Methoden der organischen Chemie, vol. IV, 1c 1980, pp. 16-26.
International Search Report No. PCT/EP2004/013814, dated Apr. 8, 2005, 3 pgs.

*Primary Examiner*—Sikarl A. Witherspoon
(74) *Attorney, Agent, or Firm*—Connolly Bove Lodge & Hutz LLP

(57) ABSTRACT

Process for preparing tricyclodecanedialdehyde by hydroformylation of dicyclopentadiene by means of a CO/$H_2$ mixture at elevated temperature and under superatmospheric pressure in the presence of a rhodium catalyst which has not been modified by means of a ligand and is homogeneously dissolved in the hydroformylation medium, wherein the hydroformylation is carried out at a pressure of from 200 to 350 bar in at least two reaction zones, with a reaction temperature of from 80 to 120° C. being set in a first reaction zone and a reaction temperature of from 120 to 150° C. being set in a reaction zone following this reaction zone, with the proviso that the reaction temperature in the subsequent reaction zone is at least 5° C. higher than in the preceding reaction zone.

19 Claims, 1 Drawing Sheet

METHOD FOR PRODUCING TRICYCLODECANDIALDEHYDE

This application is a National Phase application of PCT/EP2004/013814, filed Dec. 4, 2004, which claims priority to German patent appl. no. 103 57 718.1, filed Dec. 9, 2003.

The present invention relates to a process for preparing tricyclodecanedialdehyde by hydroformylation of dicyclopentadiene by means of a $CO/H_2$ mixture at elevated temperature and under superatmospheric pressure in the presence of a rhodium catalyst which has not been modified by means of a ligand and is homogenously dissolved in the hydroformylation medium.

In the context of the present invention, the term "tricyclodecanedialdehyde" will in the interests of simplification be used to describe the mixture of dialdehydes having the tricyclo[$5.2.10^{2,6}$]decane carbon skeleton of the formula

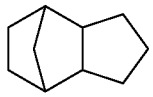

obtainable by hydroformylation of dicyclopentadiene. The trivial name "dicyclopentadiene" used for the starting compound refers to the endo, exo mixture of tricyclo[$5.2.10^{2,6}$]deca-3,8-diene of the formulae

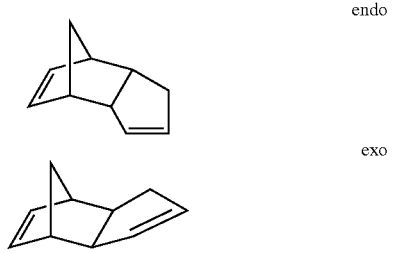

which is formed by spontaneous Diels-Alder reaction of two molecules of cyclopentadiene on its production, e.g. in cracking processes, according to reaction equation (1).

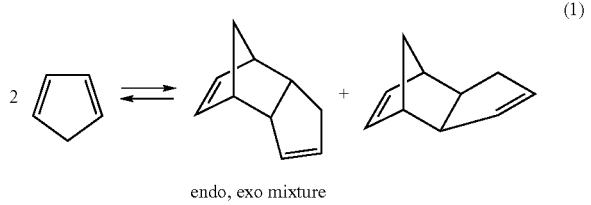

endo, exo mixture

This reaction is reversible, i.e. the dicyclopentadiene decomposes, e.g. at elevated temperatures, in a retro-Diels-Alder reaction to reform the monomer cyclopentadiene.

This retro-Diels-Alder reaction takes place under the conditions of the hydroformylation reaction, which is why, owing to the comparatively high reaction temperatures required, the hydroformylation of dicyclopentadiene to tricyclodecanedialdehyde ("TCD-dialdehyde") is advantageously not carried out using the cobalt catalysts otherwise customary for hydroformylation (cf. Cornils et al; Chemiker-Zeitung 98, 70 (1974)).

Consequently, the preparation of TCD-dialdehyde via hydroformylation of dicyclopentadiene is carried out using rhodium catalysts which are homogenously soluble in the hydroformylation medium and, owing to their higher catalyst activity, are still active at reaction temperatures lower than those employed in the case of cobalt catalysts. However, the redissociation of dicyclopentadiene into cyclopentadiene takes place, albeit at a lower rate, even at the relatively low (compared to cobalt catalysis) temperatures of the rhodium-catalyzed hydroformylation. This is of considerable relevance to the economics of TCD-dialdehyde production, since cyclopentadiene forms hydroformylation-inactive complexes with the rhodium carbonyl catalyst customarily used for the preparation of TCD, which has not been modified by means of a ligand, taking into account the fact that the rhodium is usually present in the reaction medium in amounts of less than 100 ppm by weight in hydroformylation reactions. Apart from this, the formation of such rhodium-cyclopentadienyl complexes causes a risk of losses of the valuable noble metal rhodium.

To solve these problems, measures which can be summarized under the points a) to c) below:
a) use of ligands which stabilize the rhodium catalyst and increase the hydroformylation activity,
b) increasing the concentration of rhodium catalyst which has not been modified by means of a ligand in the hydroformylation medium in order to compensate the deactivation of the rhodium catalyst by cyclopentadiene;
c) reducing the hydroformylation temperature to decrease the rate of the retro-Diels-Alder reaction to such an extent that deactivation of the rhodium catalyst by means of liberated cyclopentadiene becomes virtually negligible;
have been proposed in the past.

All these measures suffer from disadvantages which adversely affect the economics of the processes based thereon.

Re a): The hydroformylation of dicyclopentadiene using rhodium in the presence of excess triphenylphosphine (Pruett in Ann. N.Y. Acad. Sci. 295, 239, 242 (1977)) and triphenyl phosphite ligands (U.S. Pat. No. 3,499,933; Pruett in Adv. Organomet. Chem. 17, S. 32-33, (1979)) leads under mild conditions at a rhodium content of the reaction medium of 215 ppm by weight in two stages to a yield of TCD-dialdehyde of 87%. As a result of the high boiling points of TCD-dialdehyde of 150° C. at 5 mbar, corresponding to about 310° C. under atmospheric pressure, and the ligands triphenylphosphine, viz. 377° C. at atmospheric pressure, and triphenyl phosphite, viz. 360° C. at atmospheric pressure, the separation of the TCD-dialdehyde product from the ligand used in an excess over rhodium by distillation is difficult and is associated with an uneconomically high energy consumption. Furthermore, the high thermal stress leads, owing to the relatively long residence time of the TCD-dialdehyde in the distillation apparatus (separation of the dialdehyde from the ligand by flash evaporation is not possible because of the proximity of the boiling points) to product losses.

Accordingly, in the preparation of bis(aminomethyl)tricyclodecane (hereinafter referred to as "TCD-diamine") in EP-A 26 983, the rhodium catalyst modified by means of the triphenyl phosphite ligand (rhodium concentration in the reaction mixture: about 223 ppm by weight) from the hydroformylation stage is not separated off from the TCD-dialdehyde, but instead the entire hydroformylation output is used, after removal of the solvent toluene by distillation, in the reductive amination over a Raney nickel catalyst to produce TCD-diamine. In this process, rhodium losses occur as a result of adsorption of the rhodium complex on the Raney nickel catalyst.

As a further alternative to the separation of the TCD-dialdehyde from the ligand-containing hydroformylation mixture, WO 93/02024 and EP-A 1065 194 propose various liquid-liquid extraction methods, but these require a considerable outlay in terms of apparatus on the industrial scale and thus make the product expensive.

Re b): DE-A 1618 384 relates to a process for preparing TCD-dioles by hydroformylation of dicyclopentadiene over rhodium-containing catalysts which have not been modified by means of a ligand and subsequent hydrogenation of the resulting TCD-dialdehydes, with the TCD-dialdehyde-containing output from the hydroformylation stage being hydrogenated by means of the synthesis gas without the rhodium-containing catalyst being separated off and without addition of other hydrogenation catalysts by increasing the temperature to at least 200° C. According to Example 1 of DE-A 1618 384, the hydroformylation of a 25% strength by weight benzene solution of dicyclopentadiene was carried out at 130° C. and a pressure of 200 at (corresponding to 196 bar) in the presence of about 160 ppm by weight (calculated as Rh) of the rhodium catalyst produced by reaction of dirhodium trioxide ($Rh_2O_3$) with synthesis gas. After the hydroformylation was complete, the temperature of the reaction mixture was increased to 240° C., so that the TCD-dialdehyde was then hydrogenated to TCD-diol, which was obtained in a yield of about 95%.

A disadvantage of these processes is the high concentration of rhodium catalyst which has to be used in the hydroformylation to compensate for the catalyst deactivation caused by the cyclopentadiene formed under the hydroformylation conditions by means of the retro-Diels-Alder reaction. Apart from the provision of large amounts of the expensive noble metal rhodium for carrying out the process on an industrial scale, which makes the process expensive, the use of such large amounts of rhodium involves the risk of considerable rhodium losses due to deposition on the reactor walls and in pipes and apparatuses, which makes the process uneconomical. The risk of rhodium losses is additionally increased in the subsequent hydrogenation of the TCD-dialdehyde to TCD-diol by means of the same homogeneous rhodium catalyst, since decomposition of the catalytically active rhodium carbonyl compound occurs at the hydrogenation temperature of 240° C. employed. This is also shown by the fact that, according to DE-A 1618 384, the precipitated rhodium is separated off from the TCD-diol by filtration after the hydrogenation.

The hydroformylation using rhodium which has not been modified by means of a ligand involves, as mentioned above, the risk that the thermally labile rhodium catalyst (cf. U.S. Pat. No. 4,400,547) will partly decompose to metallic rhodium as a result of the thermal stress in the work-up of the hydroformylation product by distillation and the metallic rhodium will deposit on the walls of the reactor and pipes. The precipitated rhodium metal cannot be recirculated to the hydroformylation reaction, since it cannot be converted into the catalytically active rhodium compound under the hydroformylation conditions. This thermal lability shows up, in particular, when, as is the case in the work-up by distillation, the high $CO/H_2$ pressure which prevails under hydroformylation conditions and stabilizes the rhodium catalyst which has not been modified by means of a ligand has to be reduced. Moreover, decomposition of the rhodium catalyst which has not been modified by means of a ligand with deposition of metallic rhodium on the reactor walls also takes place in a $CO/H_2$ atmosphere at temperatures above 150° C. For this reason, many methods of stabilizing the rhodium catalyst which has not been modified by means of a ligand in the work-up of the hydroformylation product have been developed. An overview of such processes is given, for example, in WO 99/36382. Of course, the risk of rhodium losses is increased as the amount of rhodium catalyst which has not been modified by means of a ligand used in the hydroformylation increases.

On the other hand, if the rhodium concentration is reduced as described in EP-B 348 832, the hydroformylation rate decreases and the hydroformylation product contains not only TCD-dialdehyde but also considerable amounts of tricyclodecanemonoaldehyde ("TCD-monoaldehyde"), the product of incomplete hydroformylation of dicyclopentadiene. EP-B 348 832 relates to a process for preparing TCD-diamine by hydroformylation of dicyclopentadiene in the presence of rhodium carbonyl catalysts which have not been modified by means of a ligand and subsequent reductive amination of the resulting TCD-dialdehyde by means of hydrogen and ammonia in the presence of a hydrogenation catalyst, with the hydroformylation product, viz. TCD-dialdehyde, being reductively aminated without the rhodium catalyst being separated off. According to an example in EP-B 348 832, the hydroformylation of dicyclopentadiene is carried out in toluene solution at 135° C. and a pressure of 25 Mpa (corresponding to 250 bar) in the presence of 50 ppm by weight of rhodium and gives a product comprising TCD-dialdehyde and TCD-monoaldehyde in a ratio of about 4:1.

As the inventors' own experiments have shown (see comparative examples), the rate of the hydroformylation of dicyclopentadiene at a reaction temperature of 130° C. is very slow even at a reaction pressure of 600 bar when the rhodium concentration in the reaction mixture is reduced to 10 ppm by weight.

A disadvantage of the step following the hydroformylation in EP-B 348 832, viz. the reductive amination of TCD-dialdehyde over a heterogeneous hydrogenation catalyst, is that the TCD-dialdehyde is used without the rhodium catalyst being separated off beforehand. EP-B 348 832 indicates that a reason for this is that the separation of the TCD-dialdehyde from the hydroformylation output by distillation presents considerable difficulties which cannot be eliminated even by means of distillation processes under mild conditions, since TCD-dialdehyde tends to form relatively high molecular weight condensation products because of its high reactivity. As a consequence, the rhodium catalyst is adsorbed on the heterogeneous hydrogenation catalyst used for the reductive amination, in the case of EP-B 348 832, a nickel catalyst, and can only be recovered by work-up, i.e. destruction, of the hydrogenation catalyst. Furthermore, considerable amounts of metallic rhodium deposit on the reactor walls in the absence of the stabilizing carbon monoxide at the reaction temperature of 130° C. employed for the reductive amination.

Re c): In Brennstoff-Chemie 48, 54 (1967), Falbe et al describe the hydroformylation of dicyclopentadiene to TCD-dialdehyde by means of a rhodium carbonyl catalyst which has not been stabilized by means of a ligand and is generated in situ in the reaction mixture by the action of synthesis gas on dirhodium trioxide ($Rh_2O_3$) at a temperature of 115° C. To compensate for the slower reaction rate caused by the lower reaction temperature, a high concentration of rhodium catalyst of about 160 ppm by weight, calculated as Rh, is set in the reaction mixture. In the hydroformylation of a 20% strength by weight solution of dicyclopentadiene in THF, only a moderate yield of 61% of TCD-dialdehyde is achieved under these conditions and a pressure of 200 at (=196 bar) after a reaction time of five hours. As the inventors' own studies have shown, the hydroformylation of dicyclopentadiene to TCD-dialdehyde proceeds very slowly at 110° C. and a pressure of 280 bar at a concentration of rhodium carbonyl catalyst which has not been modified by means of a ligand in the reaction mixture of 10 ppm by weight (cf. comparative example).

TCD-dialdehyde serves as starting material for the preparation of TCD-diol or TCD-diamine. TCD-diol serves as diol component for the preparation of polyesters of unsaturated dicarboxylic acids which are either used as such for plastics reinforced with glass fibers or are processed as styrene copolymers to produce solvent-free, quick-drying surface coatings of particular hardness. Acrylic and methacrylic esters of TCD-diol which are obtainable by standard methods serve as raw materials for adhesives. Furthermore, it serves as diol component in the preparation of polyglycidyl ethers and polyurethanes. TCD-diamine is used as hardener for epoxy resins, for producing polyamide resins and as starting material for diisocyanates which are in turn processed further to produce polyurethanes. Further applications of TCD-diol and TCD-diamine are given, for example, in Cornils et al, Chemiker-Zeitung 98, 70 (1974). The synthesis of TCD-dialdehyde thus constitutes the key step in the preparation of the versatile products TCD-diol and TCD-diamine.

It was thus an object of the present invention to find an improved process for preparing TCD-dialdehyde and consequently TCD-diol and TCD-diamine which does not suffer from the disadvantages of the prior art. In particular, the process should make it possible to prepare TCD-dialdehyde economically at a good space-time yield without the risk of economically substantial rhodium losses and without the need for economically disadvantageous ligand removal operations and in this way allow the inexpensive preparation of the downstream products TCD-diol and TCD-diamine.

We have accordingly found a process for preparing tricyclodecanedialdehyde by hydroformylation of dicyclopentadiene by means of a $CO/H_2$ mixture at elevated temperature and under superatmospheric pressure in the presence of a rhodium catalyst which has not been modified by means of a ligand and is homogeneously dissolved in the hydroformylation medium, wherein the hydroformylation is carried out at a pressure of from 200 to 350 bar in at least two reaction zones, with a reaction temperature of from 80 to 120° C. being set in a first reaction zone and a reaction temperature of from 120 to 150° C. being set in a reaction zone following this reaction zone, with the proviso that the reaction temperature in the subsequent reaction zone is at least 5° C. higher than in the preceding reaction zone.

According to the invention, TCD-dialdehyde of the formula II is prepared by hydroformylation of dicyclopentadiene I by means of a $CO/H_2$ mixture in the presence of a rhodium catalyst which has not been modified by means of a ligand according to the reaction equation (2),

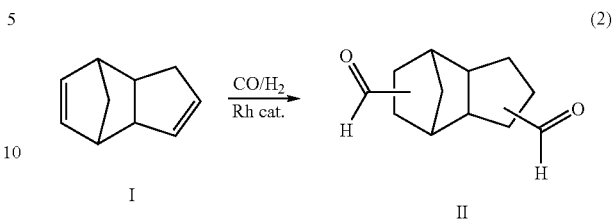

(2)

with the isolable intermediate tricyclodecenemonoaldehyde being formed during the course of the reaction and reacting further to TCD-dialdehyde.

The hydroformylation process of the invention is carried out using rhodium catalysts "which have not been modified by means of a ligand". In the present patent application, the term rhodium catalysts "which have not been modified by means of a ligand" is used to refer to rhodium hydroformylation catalysts which, in contrast to conventional rhodium hydroformylation catalysts, are not modified by means of phosphorus-containing ligands such as phosphine or phosphite ligands under the conditions of the hydroformylation. Ligands in this sense do not include carbonyl or hydrido ligands. It is assumed in the specialist literature (cf. Falbe, Ed.: New Syntheses with Carbon Monoxide, Springer, Berlin 1980, p. 38ff) that the rhodium compound $HRh(CO)_4$ is the catalytically active rhodium species in hydroformylation over rhodium catalysts which have not been modified by means of a ligand, although this has not been unambiguously proven because of the many mechanisms occurring side by side in the hydroformylation reactor. Purely in the interests of simplicity, this assumption will also be utilized here. The rhodium catalysts which have not been modified by means of a ligand are formed under the conditions of the hydroformylation reaction from rhodium compounds, e.g. rhodium salts such as rhodium(III) chloride, rhodium(III) nitrate, rhodium(I) acetate, rhodium 2-ethylhexanoate, rhodium(III) acetylacetonate, rhodium(III) sulfate or rhodium (III) ammonium chloride, from rhodium chalcogenides such as rhodium(III) oxide or rhodium(III) sulfide, from salts of oxo acids of rhodium, for example the rhodates from rhodium-carbonyl compounds such as dicarbonyl rhodium acetylacetonate, cyclooctadienerhodium acetate or chloride, in the presence of $CO/H_2$ mixtures, generally known as synthesis gas.

The process of the invention for preparing TCD-dialdehyde can be carried out in two or more, for example in three or four, reaction zones which differ in respect of the reaction temperature employed, with the hydroformylation of dicyclopentadiene being carried out at a temperature of generally from 80 to 120° C., preferably from 105 to 115° C., in a first reaction zone and the hydroformylation temperature of the output from the first reaction zone being increased to a temperature of generally from >120° C. to 150° C., preferably from 130 to 140° C., on entry into the reaction zone following this first reaction zone. The reaction zones are generally operated at a $CO/H_2$ pressure of from 200 to 350 bar, advantageously from 250 to 300 bar. The process of the invention is preferably carried out in two reaction zones.

Figure 1:
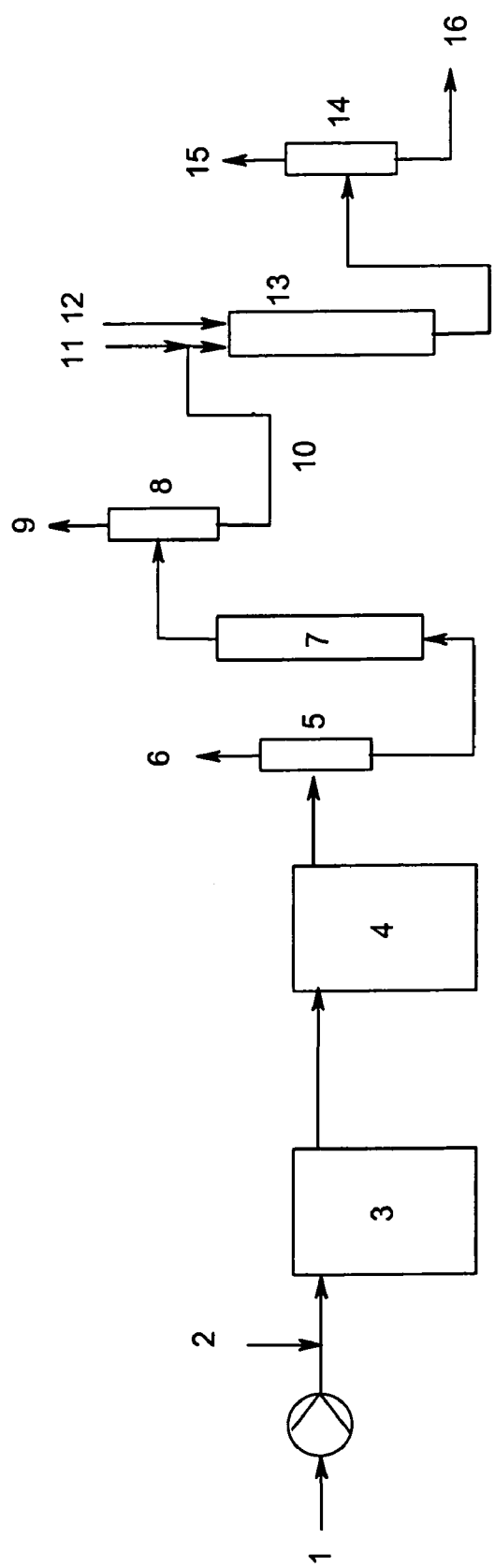
FIG. 1 describes the construction and operation of a miniplant useful for the present invention.

A reaction zone for the purposes of the present invention can comprise one or more reactors connected in series when these are operated within the temperature range specified for the reaction zone concerned. For example, the first reaction zone can consist of a single hydroformylation reactor which is operated, for example, at a temperature of 90, 100 or 110° C., or it can consist of a plurality of reactors, e.g. two or three reactors, connected in series in which the hydroformylation is carried out within the temperature range indicated for the first reaction zone, with these two or three reactors connected in series being able to be operated at the same temperature or at various temperatures within the temperature range indicated for the first reaction zone, e.g. at 90° C. in the first reactor, at 100° C. in the second reactor and at 110° C. in the third reactor of the series. This implies that a reaction zone can also comprise a plurality of reactors connected in series and/or in parallel which meet the criterion of the invention for an individual reaction zone, namely operation within the temperature range specified for the reaction zone concerned. Conversely, a single hydroformylation reactor can be segmented by means of suitable internals into a plurality of reaction compartments, with the reaction temperature being able to be set in each of the individual reaction compartments so that one or more of these reaction compartments form the first reaction zone and one or more of the following reaction compartments of the reactor form the subsequent reaction zone. What has been said above with regard to carrying out the process of the invention in the first reaction zone applies analogously to carrying out the process of the invention in the subsequent reaction zone, i.e. in the temperature range from >120° C. to 150° C.

As reactors, it is in principle possible to use all types of reactor suitable for hydroformylation reactions, for example stirred reactors, bubble column reactors as described, for example, in U.S. Pat. No. 4,778,929, circulation reactors as are claimed, for example, in EP-A 1 114 017, tube reactors in which the individual reactors of a series can have different mixing characteristics, as described, for example, in EP-A 423 769 and compartmented reactors as are claimed, for example, in EP-A 1 231 198 or by U.S. Pat. No. 5,728,893 in the process of the invention.

If a reaction zone encompasses a plurality of reactors, the same or different types of reactor can be used in this reaction zone; likewise, the same or different types of reactor can be used from reaction zone to reaction zone. Preference is given to using the same types of reactor in the individual reaction zones, e.g. gas recycle reactors or stirred vessels.

A characteristic of the hydroformylation process of the invention is thus the fact that the hydroformylation is carried out in a plurality of reaction zones, preferably two reaction zones, which are gradated with regard to the reaction temperature employed, with the first reaction zone generally being operated in the temperature range from 80 to 120° C. and the subsequent reaction zone generally being operated in the temperature range from >120° C. to 150° C. The above variants of the industrial implementation of the individual reaction zones by means of single or multiple reactors and reactor types thus represent merely possible embodiments of the process of the invention and are not, however, critical to its success. Thus, it can be advantageous in terms of capital costs to use only one reactor per reaction zone in implementing the process of the invention, but on the other hand it can be found to be more advantageous, depending on any reactors already available at the respective location of such a plant, to make use of one of the abovementioned embodiments, depending on the planned plant capacity and available reactor capacity.

In general, the hydroformylation output from the first reaction zone is passed without further work-up to the subsequent reaction zone.

In general, a pressure of from 200 to 350 bar, preferably from 250 to 300 bar, is employed in the two reaction zones in the hydroformylation process of the invention. It is possible to employ a lower or higher pressure. The pressure is usually generated by injection of the $CO/H_2$ mixture required for the hydroformylation into the reactors.

$CO/H_2$ mixtures having $CO/H_2$ molar ratios of from 1:10 to 10:1, preferably from 1:2 to 2:1, can be used in the hydroformylation process of the invention. Particular preference is given to using a synthesis gas having a $CO/H_2$ molar ratio as is produced in industrial synthesis gas plants. The $CO/H_2$ molar ratio of such synthesis gases is generally in the range from 39:61 to 41:59 $CO/H_2$.

The hydroformylation process of the invention can be carried out in the presence or absence of solvents. Although there are in principle no restrictions with regard to the solvents customarily used in hydroformylation processes when a solvent is used in the process of the invention, preference is given to using solvents which can easily be separated by distillation from the relatively high-boiling TCD-dialdehyde or do not have to be separated off in the process of the invention. The latter type of solvents includes TCD-dialdehyde itself and TCD-diol. Other suitable conventional solvents are aromatics such as benzene, toluene and xylene or mixtures thereof, hydrocarbons or mixtures of hydrocarbons, esters of aliphatic carboxylic acids, e.g. ethyl acetate, ethers such as tert-butyl methyl ether, tert-butyl ethyl ether and tetrahydrofuran, likewise alcohols such as methanol, ethanol, n-propanol, isopropanol, n-butanol, isobutanol, tert-butanol, pentanol and also ketones such as acetone or methyl ethyl ketone. "Ionic liquids" can also advantageously be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, with the counterion in each case being able to be, for example, the tetrafluoroborate, acetate, tetrachloroaluminate, hexafluorophosphate, chloride or tosylate anion. These ionic liquids can be separated off from the hydroformylation mixture by phase separation.

The rhodium concentration to be employed is not critical for the process of the invention, i.e. it is in principle possible to work both with high and with low rhodium concentrations without this having adverse effects on the hydroformylation result. The rhodium concentration in the liquid reaction mixture of the hydroformylation process in the process of the invention is advantageously set to from 2 to 20 ppm by weight, particularly preferably from 4 to 10 ppm by weight, in each case calculated as Rh. It is of course also possible to employ higher rhodium concentrations.

The procedure according to the invention using gradated temperatures in two or more reaction zones surprisingly makes it possible, despite very low rhodium concentrations in the reaction mixture of the hydroformylation very rhodium concentrations in the reaction mixture of the hydroformylation, to achieve very good space-time yields in the preparation of TCD-dialdehyde from dicyclopentadiene.

This minimizes the risk of economically disadvantageous rhodium losses as a result of decomposition of the uncomplexed rhodium catalyst. Without wishing to be tied to the following theory in any form, it is assumed that the strained double bond of the cyclopentadienyl ring of the dicyclopentadiene is firstly hydroformylated at the low reaction temperature employed in the first reaction zone, as a result of which the ring system can no longer undergo a retro-Diels-Alder reaction, which is why the rate of the hydroformylation of the relatively unreactive second double bond can then be accelerated in the second reaction zone by increasing the temperature without the risk of forming hydroformylation-inactive cyclopentadienyl complexes of the rhodium.

Since the starting material dicyclopentadiene is in the form of a mixture of endo and exo isomers, attack by the rhodium catalyst can in each case occur both at geometrically different positions of the two double bonds and also in stereochemically different ways from above or below relative to the plane of the ring system, so that the hydroformylation product obtained is a mixture of regioisomeric and stereoisomeric dialdehydes which, as mentioned at the outset, is referred to as TCD-dialdehyde for the purposes of the present patent application. This mixture can either be traded as such or be subjected to subsequent reactions such as hydrogenation to TCD-diol or reductive amination to TCD-diamine.

The process of the invention can be carried out either batchwise or continuously, with preference being given to it being carried out continuously.

The process of the invention is generally carried out by the liquid discharge method. Here, the liquid hydroformylation mixture is taken off from the first reaction zone and introduced in liquid form into the subsequent reaction zone. Work-up of the hydroformylation output from the first reaction zone before it is introduced into the subsequent reaction zone is possible, but the hydroformylation output from the first reaction zone is generally passed without work-up to the second reaction zone. The second reaction zone is operated at the selected reaction temperature which is different from that of the first reaction zone. The reaction in the second reaction zone can be carried out at the same pressure as in the first reaction zone or at a lower or higher pressure. In general, the reaction in the second reaction zone is carried out under the same pressure or approximately the same pressure as in the first reaction zone.

The liquid reaction mixture from the second reaction zone can, if desired, be passed to one or more further reaction zones, but it is preferably worked up. To carry out the work-up, the output from the second reaction zone is taken continuously from the hydroformylation reactor and depressurized into a depressurization vessel to a pressure which is generally from 1 to 35 bar, preferably from 3 to 10 bar, lower than that prevailing in the hydroformylation reactor to separate off gases dissolved therein, e.g. unreacted $CO/H_2$ mixture, $CO_2$ and nitrogen. The gases liberated in the depressurization vessel can, if desired, be recirculated to one or both of the preceding reaction zones, in which case it may be advantageous to subject this gaseous recycle stream to a scrub or an intermediate condensation in a heat exchanger to remove entrained TCD-aldehyde and/or dicyclopentadiene and/or tricyclodecane or to discharge a substream of this recycle stream to avoid accumulation of inert gases in the reaction system. The liquid product mixture obtained in the depressurization vessel can then, if appropriate after prior removal of the rhodium catalyst by, for example, methods as described in WO 99/36382, be depressurized via one or more depressurization stages, with the number of depressurization stages generally depending on the configuration in terms of apparatus of the plant concerned, to atmospheric pressure or, if the TCD-dialdehyde is subsequently to be processed further to TCD-diol or TCD-diamine, to the pressure to be employed for the subsequent reaction. If isolation of the TCD-dialdehyde is desired, any solvent added to the reaction mixture is advantageously removed in a conventional fashion, for example by distillation or by phase separation if an ionic liquid is used.

In a preferred embodiment of the process of the invention, the work-up of the liquid hydroformylation output from the second reaction zone is carried out by firstly depressurizing it as described above into a depressurization vessel to a pressure which is from 5 to 30 bar abs., preferably from 5 to 10 bar abs., lower than that prevailing in the second reaction zone, passing the resulting product liquid which is still under a high $CO/H_2$ pressure over an ion exchanger to separate off the rhodium catalyst and subsequently depressurizing the demetallized product mixture in one or more depressurization stages either to atmospheric pressure or to the pressure required for any subsequent reaction, e.g. hydrogenation to TCD-diol or reductive amination to TCD-diamine. The removal of the rhodium catalyst is advantageously carried out as described in DE-A 1954 315 or WO 02/20451 over an ion exchange resin which is based on styrene-divinylbenzene copolymers and contains primary, secondary, tertiary or quaternary amine groups in base form, e.g. Amberlite® IR45 or Dowex® 4. Macroreticular ion exchange resins such as Amberlyst® A21, Lewatit® MP62, Lewatit® MP64, Imac® A20, Zerolit® G, Amberlite® IRA93, Amberlyst® A26 or Amberlyst® A27 are particularly useful. The rhodium can likewise be separated off from the hydroformylation output using macroporous, macroreticular ion exchange resins based on styrene-divinylbenzene copolymers and containing sulfonic acid groups, e.g. the ion exchanger Amberlyst® 15 mentioned for this purpose in U.S. Pat. No. 5,208,194. Separating off the rhodium catalyst from the hydroformylation product at a still relatively high pressure has the advantage that the rhodium catalyst is stabilized sufficiently by the $CO/H_2$ mixture still dissolved in the product mixture to prevent decomposition of the rhodium carbonyl compound with deposition of elemental rhodium on the walls of the apparatuses and the rhodium losses associated therewith. The rhodium can be recovered virtually quantitatively from the ion exchange resins laden therewith in a simple manner, for example by ashing as described in U.S. Pat. No. 5,208,194 and WO 02/20451.

In another preferred embodiment of the process of the invention, the liquid hydroformylation output from the second reaction zone can be depressurized to about 1-10 bar, preferably to atmospheric pressure. The temperature of the liquid hydroformylation output can be reduced to generally from 40 to 100° C., preferably to from 60 to 90° C., by additional cooling, which likewise achieves stabilization of the temperature-sensitive rhodium catalyst. Depressurization can be carried out in one or more stages. The liquid hydroformylation output which has been depressurized and cooled in this way can then be treated with a suitable ion exchanger in the above-described manner to separate off the rhodium catalyst.

The process of the invention for preparing TCD-dialdehyde by hydroformylation of dicyclopentadiene can also be utilized in a completely analogous manner for the hydroformylation of the tricyclopentadiene isomers IIIa and IIIb to form the corresponding pentacyclopentadecanedialdehydes IVa and IVb.

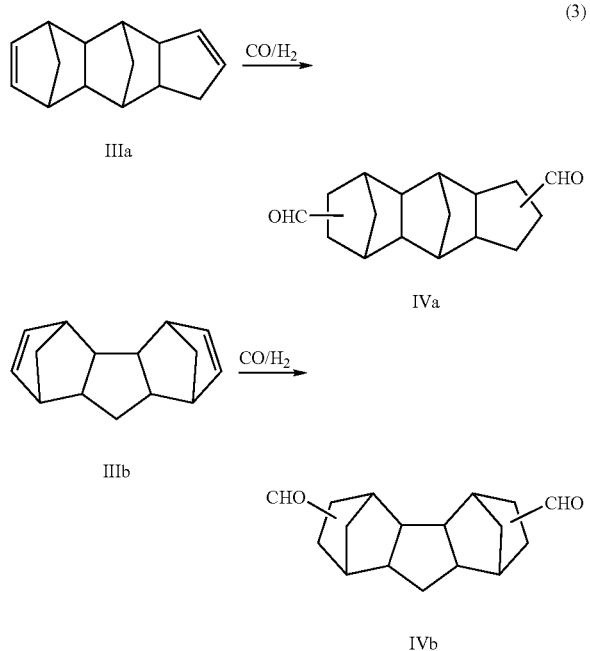

The pentacyclopentadecanedimethanols and diaminomethyl derivatives which can be obtained from the pentacyclopentadecanedialdehydes in an analogous manner by hydrogenation or reductive amination are used in applications similar to those for TCD-diol or TCD-diamine.

As already mentioned, the preparation of TCD-dialdehyde is the key step for the economical preparation of the downstream products 3(4),8(9)-dimethyloltricyclo-[5.2.10$^{2,6}$]decane (TCD-diol) and 3(4),8(9))-diaminomethyltricyclo[5.2.10$^{2,6}$]decane (TCD-diamine) which can be obtained in a conventional manner by hydrogenation or reductive amination of TCD-dialdehyde. Consequently, the economics of the process for preparing TCD-dialdehyde has a critical influence on the economics of the processes for preparing TCD-diol and TCD-diamine.

The present invention therefore also provides a process for preparing tricyclodecanedimethanol by hydroformylation of dicyclopentadiene by means of a CO/H$_2$ mixture at elevated temperature and under superatmospheric pressure in the presence of a rhodium catalyst which has not been modified by means of a ligand and is homogeneously dissolved in the hydroformylation medium to form tricyclodecanedialdehyde, subsequent separation of the rhodium catalyst from the tricyclodecanedialdehyde and hydrogenation of the tricyclodecanedialdehyde by means of a gas comprising molecular hydrogen at elevated temperature and under superatmospheric pressure over a heterogeneous catalyst, wherein the hydroformylation is carried out at a pressure of from 200 to 350 bar in at least two reaction zones, with a reaction temperature of from 80 to 120° C. being set in a first reaction zone and a reaction temperature of from 120 to 150° C. being set in a reaction zone following this reaction zone, with the proviso that the reaction temperature in the subsequent reaction zone is at least 5° C. higher than in the preceding reaction zone.

According to the invention, the key step for the economical preparation of TCD-diol, namely the synthesis of TCD-dialdehyde, is thus carried out as in the process of the invention for preparing TCD-dialdehyde.

As already mentioned in the discussion of the hydroformylation process of the invention, the output from the hydroformylation process, which comprises essentially TCD-dialdehyde, the rhodium catalyst and any solvent added in the hydroformylation, can, after the rhodium catalyst has been separated off, be fed directly to the hydrogenation to form TCD-diol. Any solvent present in the hydroformylation output can be separated off from the hydroformylation output before the latter is passed to the hydrogenation, particularly when ionic liquids are used as solvents. Preference is given, particularly when using conventional solvents, to feeding the hydroformylation output directly into the hydrogenation reactor without prior removal of the solvent.

As gases comprising molecular hydrogen, either hydrogen or gas mixtures of hydrogen and a gas which is inert under the hydrogenation conditions, e.g. nitrogen, carbon dioxide, argon and/or methane, can be used in the process of the invention. Preference is given to using only hydrogen.

The hydrogenation catalyst to be used for the hydrogenation of TCD-dialdehyde to TCD-diol is not subject matter of the present invention. Consequently, the listing of suitable hydrogenation catalysts below serves merely to exemplify the invention and has only an illustrative but not restrictive character.

As hydrogenation catalysts for the hydrogenation of TCD-dialdehyde to TCD-diol, it is possible to use virtually all heterogeneous catalysts suitable for the hydrogenation of carbonyl groups, for example those described in Houben-Weyl, Methoden der Organischen Chemie, Volume IV, 1c, p. 16-26, Thieme-Verlag, Stuttgart, 1980. In the process of the invention, the hydrogenation catalysts can be present in the reactor as a fixed bed or in mobile form, e.g. in a fluidized bed.

Preference is given to using heterogeneous hydrogenation catalysts which comprise one or more elements of groups Ib, VIb, VIIb and VIIIb of the Periodic Table of the Elements. These catalysts can further comprise one or more elements from groups Ia, IIa, IIIa, IVa and Va of the Periodic Table of the Elements to improve their catalytic activity and selectivity. Preferred catalysts are, in particular, ones which comprise, as catalytically active components, for example copper, chromium, rhenium, cobalt, nickel, rhodium, ruthenium, iridium, palladium, iron or platinum or mixtures of a plurality of these elements and also, if appropriate, further components which influence their catalytic activity and selectivity, e.g. indium, tin or antimony. The hydrogenation of TCD-dialdehyde is particularly preferably carried out using hydrogenation catalysts comprising cobalt, nickel and/or copper.

As heterogeneous catalysts, it is possible to use either precipitated catalysts or conventional supported catalysts which have been produced by application of the catalytically active components to a support material.

The precipitated catalysts can be produced by precipitating their catalytically active components from salt solutions thereof, in particular from the solutions of nitrates and/or acetates thereof by addition of solutions of alkali metal and/or alkaline earth metal hydroxides and/or carbonates, e.g. as sparingly soluble hydroxides, hydrated oxides, basic salts or carbonates, subsequently drying the resulting precipitate and then converting it by calcination at generally from 300 to 700° C., in particular from 400 to 600° C., into the corresponding oxides, mixed oxides and/or mixed-valence oxides which are reduced by treatment with hydrogen or hydrogen-containing gases at generally from 50 to 700° C., in particular from 100 to 400° C., to the respective metals and/or oxidic compounds having a low oxidation state and converted into their actual catalytically active form. In place of hydrogen, it is also possible to use other reducing agents, e.g. hydrazine, for this purpose, but preference is given to using hydrogen. The reduction is generally carried out until virtually no more hydrogen is consumed. In the production of precipitated catalysts comprising a support material, the precipitation of the catalytically active components can be carried out in the presence of the respective support material. However, the catalytically active components can advantageously also be precipitated simultaneously with the support material from the appropriate salt solutions. Suitable support materials are, for example, the oxides of aluminum, of titanium, zinc oxide, zirconium dioxide, silicon dioxide, clay minerals, e.g. montmorrillonites, silicates such as magnesium or aluminum silicates, kieselguhr or zeolites such as ZSM-5 or ZSM-10 zeolites. It is also possible to use mixtures of such support materials. If desired, the dried precipitate from the precipitation can be admixed with shaping aids such as graphite, talc or stearin and/or with pore formers such as cellulose, methylcellulose, starch, wax, paraffin and/or a polyalkylene glycol and pressed or extruded to form shaped catalyst bodies such as pellets, spheres, rings or extrudates prior to calcination.

Preference is given to using hydrogenation catalysts in which the metals or metal compounds which catalyze the hydrogenation have been deposited on a support material. Apart from the abovementioned precipitated catalysts which comprise a support material in addition to the catalytically active components, supported catalysts in which the catalytically active components have been applied to a support material, e.g. by impregnation, are generally also particularly useful for the preparation of TCD-diol.

The way in which the catalytically active metals are applied to the support is generally not critical and the application can be carried out in various ways. The catalytically active metals can be applied to these support materials by, for example, impregnation with solutions or suspensions of the salts or oxides of the respective elements, drying and subsequent reduction of the metal compounds to the respective metals or compounds having a low oxidation state by means of a reducing agent, for example by means of hydrogen, hydrogen-containing gases or hydrazine, preferably by means of hydrogen-containing gases. The reduction of the metal compounds deposited on the support material can be carried out under the same conditions as have been indicated above in the case of the precipitated catalysts. Another possible way of applying the catalytically active metals to these supports is to impregnate the supports with solutions of salts which can readily be decomposed thermally, e.g. with nitrates or complexes which can readily be decomposed thermally, e.g. carbonyl or hydrido complexes of the catalytically active metals, and to heat the support which has been impregnated in this way to temperatures of from 300 to 600° C. in order to thermally decompose the adsorbed metal compounds. This thermal decomposition is preferably carried out under a protective gas atmosphere. Suitable protective gases are, for example, nitrogen, carbon dioxide, hydrogen or noble gases. Furthermore, the catalytically active metals can be deposited on the catalyst support by vapor deposition or by flame spraying. In this case, metal wire meshes or metal foils can also serve as support materials.

The amount of catalytically active metals present in the supported catalysts is in principle not critical to the success of the hydrogenation. It will be obvious to a person skilled in the art that higher contents of catalytically active metals in the supported catalysts can lead to higher space-time yields than lower contents. Use is generally made of supported catalysts whose catalytically active metal content is from 0.1 to 90% by weight, preferably from 0.5 to 40% by weight, based on the total catalyst. Since these contents are based on the total catalyst including support material but the various support materials have very different specific gravities and specific surface areas, the contents can be below or above the figures quoted without this having an adverse effect on the result of the process of the invention. Of course, a plurality of catalytically active metals can also have been applied to the respective support material. Furthermore, the catalytically active metals can be applied to the support by, for example, the methods of DE-A 25 19 817, EP-A 147 219 and EP-A 285 420. In the catalysts described in these documents, the catalytically active metals are present as alloys which are produced by thermal treatment and/or reduction of the salts or complexes of the abovementioned metals deposited on a support, e.g. by impregnation.

As support materials, it is generally possible to use the oxides of aluminum, of titanium, zinc oxide, zirconium dioxide, silicon dioxide, clay minerals, e.g. montmorillonites, silicates such as magnesium or aluminum silicates, zeolites such as ZSM-5 or ZSM-10 zeolites and also activated carbon. Preferred support materials are aluminum oxides, titanium dioxides, silicon dioxide, zirconium dioxide, kieselguhr and activated carbon. It is of course also possible to use mixtures of various support materials as supports for hydrogenation catalysts.

As hydrogenation catalysts which can be used for the hydrogenation of TCD-dialdehyde to TCD-diol, the following may be mentioned by way of example: cobalt on activated carbon, cobalt, cobalt on silicon dioxide, cobalt on aluminum oxide, iron on activated carbon, manganese on activated carbon, nickel, nickel on silicon dioxide, nickel on kieselguhr, copper on activated carbon, copper on silicon dioxide, copper on aluminum oxide, copper chromite, copper/nickel precipitated catalysts and also the catalysts described in DE-A 3932 332, WO 01/87809, EP-A 44 444, EP-A 224 872, DE-A 39 04 083, DE-A 23 21 101, EP-A 415 202, DE-A 23 66 264, DE-A 2628 987, EP-A 394 842 and EP-A 100 406.

The hydrogenation conditions, i.e. pressure and temperature, are subject to no particular requirements in respect of the starting material TCD-dialdehyde and the hydrogenation product TCD-diol. In view of the wide variety of different suitable hydrogenation catalysts, some of which are commercially available and some of which can be produced according to the published prior art, it is usual firstly to choose hydrogenation conditions which correspond to the optimum operating conditions for the hydrogenation catalyst used in each case and which are disclosed in the case of commercial catalysts in the relevant operating instructions or in the case of catalysts known from the published prior art are disclosed in the documents concerned. The hydrogenation conditions set in this way can then be optimized further in routine tests.

The hydrogenation of TCD-dialdehyde can be carried out in stirred vessels by means of a suspension of fine hydrogenation catalyst particles, e.g. Raney nickel or Raney cobalt, but the hydrogenation catalyst is preferably installed in a fixed bed in the hydrogenation reactor over which the reaction mixture can be passed in the upflow or downflow mode. Suitable reactors for this purpose are, for example, tube reactors or loop reactors through which the reaction mixture is circulated over the fixed catalyst bed by means of a pump. In such a case, a cooling facility, e.g. in the form of a heat exchanger, can advantageously be installed in the reactor loop to remove the heat of hydrogenation. In view of the large quantity of heat evolved in the hydrogenation, it can also be advantageous to carry out the hydrogenation stepwise in two or more hydrogenation reactors connected in series, if desired with intermediate cooling of the reaction mixture before it enters the second reactor and to carry out the hydrogenation only to partial conversion of the TCD-dialdehyde in the first reactor.

To suppress secondary reactions such as acetal formation or aldol condensation, up to 10% by weight of water can be added to the TCD-dialdehyde before it is fed into the hydrogenation reactor.

After depressurization of the hydrogenation output and removal of any solvents and water present therein by distillation, the TCD-diol can be purified by distillation, preferably under reduced pressure. In a preferred embodiment of the process, the TCD-diol can be freed of low-boiling impurities by means of steam distillation, if desired under reduced pressure. In this purification method, the low boilers are stripped from the crude TCD-diol product by means of steam. Since the starting material TCD-dialdehyde is used in the form of a mixture of isomers in the hydrogenation, the TCD-diol is likewise obtained as a mixture of isomers.

The present invention further provides a process for preparing diaminomethyltricyclodecane by hydroformylation of dicyclopentadiene by means of a $CO/H_2$ mixture under superatmospheric pressure and at elevated temperature in the presence of a rhodium catalyst which has not been modified by means of a ligand and is homogeneously dissolved in the hydroformylation medium, subsequent separation of the rhodium catalyst from the tricyclodecanedialdehyde and reductive amination of the tricyclodecanedialdehyde at elevated temperature and under superatmospheric pressure over a heterogeneous catalyst in the presence of a gas comprising molecular hydrogen and ammonia, wherein the hydroformylation is carried out at a pressure of from 200 to 350 bar in at least two reaction zones, with a reaction temperature of from 80 to 120° C. being set in a first reaction zone and a reaction temperature of from 120 to 150° C. being set in a reaction zone following this reaction zone, with the proviso that the reaction temperature in the subsequent reaction zone is at least 5° C. higher than in the preceding reaction zone.

According to the invention, the key step for the economical preparation of TCD-diamine, namely the hydroformylation of dicyclopentadiene to TCD-dialdehyde, is thus carried out as in the hydroformylation process of the invention.

As already mentioned in the discussion of the hydroformylation process of the invention, the output from the hydroformylation process, which comprises essentially TCD-dialdehyde, the rhodium catalyst and any solvent added in the hydroformylation, can, after the rhodium catalyst has been separated off, be fed directly to the reductive amination to form TCD-diamine. Any solvent present in the hydroformylation output can be separated off from the hydroformylation output before the latter is passed to the amination, particularly when ionic liquids are used as solvents. Preference is given, particularly when using conventional solvents, to feeding the hydroformylation output directly into the amination reactor without prior removal of the solvent.

If TCD-diol has been used as solvent in the hydroformylation, this is likewise converted into TCD-diamine over the amination catalyst. This is based on the fact that the amination catalysts are by nature hydrogenation catalysts which as such also bring about the dehydrogenation of alcohols to aldehydes in an equilibrium reaction. Any TCD-diol present in the TCD-dialdehyde is consequently firstly dehydrogenated over the amination catalyst to TCD-dialdehyde which forms an imine with the ammonia fed into the amination reactor and this imine is then hydrogenated over the amination catalyst to form the amine. Accordingly, hydrogen is consumed in a stoichiometric amount for the reduction of the imine in the reductive amination of TCD-dialdehyde, while in the amination of TCD-diol hydrogen is firstly liberated as an intermediate as a result of dehydrogenation and is then consumed again for the hydrogenation of the imine to amine in the subsequent reaction. The two reactions proceed in parallel over the amination catalyst. Even though formally no hydrogen is consumed in the amination of TCD-diol, the presence of molecular hydrogen is necessary in carrying out the amination of TCD-diol in order to activate the amination catalyst. It can be seen from the above that, if desired, mixtures of TCD-dialdehyde with TCD-diol can be used in the amination in place of TCD-dialdehyde.

The reductive amination of TCD-dialdehyde to TCD-diamine by means of gases comprising molecular hydrogen and ammonia can be effected in a conventional manner at a pressure of generally from 1 to 400 bar, preferably from 10 to 250 bar and particularly preferably from 30 to 200 bar, and a reaction temperature of generally from 50 to 250° C., preferably from 80 to 200° C. and particularly preferably from 100 to 200° C. As gases comprising molecular hydrogen, either hydrogen or gas mixtures of hydrogen and a gas which is inert under the hydrogenation conditions, e.g. nitrogen, carbon dioxide, argon and/or methane, can be used in the process of the invention.

The ammonia can be used in a stoichiometric amount based on the two carbonyl groups present in the TCD-dialdehyde, but the ammonia is generally introduced in a from 5 to 250-fold, preferably from 10 to 100-fold and particularly preferably from 25 to 80-fold, molar excess per mole of carbonyl group to be aminated in order to reduce the formation of secondary or tertiary amines. The molecular hydrogen is generally added in an amount of from 0.5 to 40 mol, preferably from 2 to 30 mol and particularly preferably from 4 to 30 mol, per mole of carbonyl group to be aminated. Even if TCD-diol is present in the starting material, it is usual to employ a hydrogen excess of from 0.5 to 40 mol, preferably from 2 to 30 mol, in particular from 4 to 30 mol, per mole of methylol group to be aminated.

The heterogeneous catalyst used for the reductive amination is not subject matter of the present invention. The reductive amination of TCD-dialdehyde can be carried out using all heterogeneous catalysts customarily used for reductive aminations. Since the heterogeneous catalysts for the reductive amination are hydrogenation catalysts, the reductive amination of TCD-dialdehyde or TCD-diol to TCD-diamine can be carried out using virtually the same catalysts mentioned above for the hydrogenation of TCD-dialdehyde to TCD-diol.

Preference is given to using catalysts whose active catalyst composition comprises up to 100% by weight of at least one element or at least one compound of an element of group VIII of the Periodic Table of the Elements, i.e. from the group consisting of Fe, Ru, Os, Co, Rh, Ir, Ni, Pd and Pt. The active catalyst composition can, in a preferred embodiment, further comprise up to 50% by weight of at least one element or at least one compound of an element of group IB of the Periodic Table of the Elements, i.e. from the group consisting of Cu, Ag and Au, preferably Cu. The amount of metal or compound of a metal of group IB is, in a further preferred embodiment, from 1 to 30% by weight, in particular from 10 to 25% by weight, based on the total amount of active catalyst composition.

The catalysts can be used as precipitated catalysts or in supported form. When supported catalysts are used, the proportion of support is generally from 10 to 90% by weight, based on the total mass of the catalyst (active composition plus support).

As supports, it is possible to use all known suitable supports, for example activated carbon, silicon carbide or metal oxides. The use of metal oxides is preferred. Among the metal oxides, preference is given to using aluminum oxide, silicon dioxide, titanium dioxide, zirconium dioxide, zinc oxide, magnesium oxide or mixtures thereof, which may, if appropriate, be doped with alkali metal oxides and/or alkaline earth metal oxides. Particular preference is given to γ-aluminum oxide, silicon dioxide, zirconium dioxide or titanium dioxide or mixtures thereof, in particular $Al_2O_3$. The supports can be used in any form, for example as extrudates (in the form of extruded rods), pellets, tablets, monoliths, woven meshes, knitted meshes or in powder form. The supported catalysts can be produced by generally known methods.

The reductive amination of TCD-dialdehyde can be carried out in conventional reactors customarily used for reductive amination reactions. For example, the preparation of TCD-diamine can be carried out in stirred vessels using finely divided catalysts such as Raney nickel or Raney cobalt suspended in the reaction mixture. The amination catalyst is preferably located in one or more fixed beds which can be installed in conventional tube or loop reactors and over which the liquid reaction mixture can be passed in the upflow or downflow mode. To remove the heat of reaction evolved in the reductive amination, the reactors are advantageously equipped with cooling facilities, for example heat exchangers. In view of the heat of reaction evolved in the reductive amination, it can also be advantageous to carry out the reductive amination stepwise in two or more reactors connected in series or over a plurality of fixed beds, if desired with intermediate cooling of the reaction mixture before it enters the next reactor or the next fixed catalyst bed, and in such a case to carry out the reaction only to partial conversion of the TCD-dialdehyde in the preceding reactor or over the preceding fixed bed.

After depressurization of the output from the amination reactor and, if desired, recirculation of unreacted hydrogen and ammonia to the reductive amination and, if appropriate, removal of solvent present in the reaction mixture and water formed in the reductive amination by distillation, the TCD-diamine can be purified if desired, preferably under reduced pressure. Since the starting material TCD-dialdehyde and possibly TCD-diol is/are used in the form of a mixture of isomers in the reductive amination, the TCD-diamine is likewise obtained as a mixture of isomers.

Primary and secondary amines, e.g. $C_1$-$C_{10}$-monoalkylamines, N,N—$C_1$-$C_{10}$-dialkylamines or arylamines, preferably $C_1$-$C_4$-monoalkylamines or N,N—$C_1$-$C_4$-dialkylamines can be used in place of ammonia as starting material in the reductive amination, which then results in formation of TCD-diamines which are correspondingly substituted on the nitrogen atom.

The invention is illustrated by the following examples and comparative examples.

Analysis:

All product mixtures were analyzed by gas chromatography and the proportions of the individual components are reported in % by area. Differences in the sensitivity of the detection of the individual components by the GC detector were not corrected by calibration.

COMPARATIVE EXAMPLE 1

Hydroformylation of Dicyclopentadiene at 130° C. and 600 Bar 5 mg of $Rh(CO)_2(acac)\hat{=}47$ ppm by weight were dissolved in 100 g of dicyclopentadiene, the mixture was placed in an autoclave and the autoclave was pressurized with 200 bar of $CO/H_2$ (1:1). The autoclave was then heated to 130° C. and, after this temperature had been reached, the pressure was set to 600 bar by means of $CO/H_2$ (1:1). The temperature and the pressure were maintained for 10 hours. After cooling, a sample was analyzed by means of gas chromatography:

| | |
|---|---|
| Dicyclopentadiene | 0.3% by area |
| TCD-Monoaldehyde | 65.2% by area |
| TCD-Dialdehyde | 5.9% by area |
| Sum of high boilers | 27.2% by area |
| % by area = | area of an individual peak in the gas chromatogram divided by the total area of all peaks × 100 |
| acac = acetylacetonate | |

Comparative example 1 shows that even at a rhodium concentration of 47 ppm by weight at a relatively high hydroformylation temperature of 130° C. and even under a very high $CO/H_2$ pressure of 600 bar, only little TCD-dialdehyde is formed in the hydroformylation of dicyclopentadiene even after a reaction time of 10 hours and the hydroformylation reaction stays at the TCD-monoaldehyde stage.

COMPARATIVE EXAMPLE 2

Hydroformylation of Dicyclopentadiene at 110° C. and 280 Bar 500 g of dicyclopentadiene and 400 g of toluene were placed in an autoclave and the autoclave was pressurized with 20 bar of $CO/H_2$ (1:1). The autoclave was then heated to 110° C. and the pressure was set to 220 bar by means of $CO/H_2$ (1:1). The catalyst solution consisting of 25.8 mg of $Rh(CO)_2(acac)$ ($\hat{=}12$ ppm by weight of Rh based on the total reaction mixture) in 100 g of toluene was added via a lock and the pressure was set to 280 bar. A temperature of 110° C. and a pressure of 280 bar were maintained over a period of ten hours.

Samples were taken from the autoclave and analyzed by means of gas chromatography (figures in % by area, toluene excluded from the calculation):

| Compound | After 1 h | After 2 h |
|---|---|---|
| Dicyclopentadiene | 1.7 | 0.3 |
| TCD-Monoaldehyde | 91.5 | 71.5 |
| TCD-Dialdehyde | 3.9 | 22.8 |
| Sum of high boilers | 1.3 | 1.6 |

Comparative example 2 demonstrates that the hydroformylation of dicyclopentadiene proceeds very slowly and with only a very low space-time yield at a relatively low reaction temperature of 110° C. at a CO/H$_2$ pressure of 280 bar and an Rh concentration of 12 ppm by weight. After a reaction time of two hours, the TCD-dialdehyde/TCD-monoaldehyde ratio is only 1:3.

EXAMPLE 3 (According to the Invention)

Hydroformylation of Dicyclopentadiene at 110/130° C. and 280 Bar 500 g of dicyclopentadiene and 400 g of toluene were placed in an autoclave and the autoclave was pressurized with 20 bar of CO/H$_2$ (1:1). The autoclave was then heated to 110° C. and the pressure was set to 220 bar by means of CO/H$_2$ (1:1). The catalyst solution consisting of 25.8 mg of Rh(CO)$_2$ (acac) (=12 ppm by weight based on the total reaction mixture) in 100 g of toluene was added via a lock and the pressure was set to 280 bar; this pressure was maintained over the entire reaction time. In the first hour, the temperature was maintained at 110° C., and the temperature was subsequently increased to 130° C. and the reaction was continued for a further three hours.

Samples were taken from the autoclave and analyzed by means of gas chromatography (figures in % by area, toluene excluded from the calculation):

| Compound | After 1 h | After 2 h | After 2.5 h |
|---|---|---|---|
| Dicyclopentadiene | 0.3 | 0.1 | 0.1 |
| TCD-Monoaldehyde | 97.2 | 9.8 | 2.9 |
| TCD-Dialdehyde | 2.1 | 89.9 | 93.4 |
| Sum of high boilers | 9.6 | 2.3 | 0.2 |

EXAMPLE 4 (According to the Invention)

Continuous Hydroformylation of Dicyclopentadiene in a Miniplant with Subsequent Hydrogenation of the TCD-dialdehyde to TCD-diol The description of the construction and operation of the miniplant refers to the schematic drawing attached to the patent application.

The dicyclopentadiene dissolved in pentanol (1) was conveyed by means of a pump into the reactor 3. The synthesis gas (2; CO:H2=1:1) was additionally metered into the olefin stream. The catalyst had previously been dissolved in the olefin as Rh(CO)$_2$ (acac) (acac=acetylacetonate). From the first reactor 3, the reaction mixture traveled to the second reactor 4 and from there into the separator 5. There, an offgas stream was taken off at the top and the liquid phase at the bottom was passed through the ion exchanger bed 7. After the ion exchanger bed 7, the reaction mixture went to the low-pressure separator 8 where gas phase (9) and liquid phase (10) were again separated. The liquid phase 10 was fed into a hydrogenation reactor 13. Water (11) and hydrogen (12) were additionally metered into this reactor. The output from the hydrogenation reactor 13 was freed of gas in a gas separator 14 and the crude alcohol 16 was taken off.

The miniplant was operated under the following conditions:
Olefin feed 1
400 g/h of dicyclopentadiene:pentanol=50:50 w/w
10 ppm by weight of rhodium
Reactor 3
110° C., 280 bar
Reactor 4
130° C., 280 bar
Offgas 6 and 9
About 50 standard l/h
 The residence time in both reactors was in each case about 3 hours.
Ion exchanger bed 7
80° C., 7 bar
Amberlyst® A21
Water feed 11
40 g/h
Hydrogenation reactor 13
170 to 180° C., 280 bar Two hydrogenation catalysts were installed in fixed beds in the hydrogenation reactor operated in the downflow mode. The first catalyst bed closest to the reactor inlet comprised 1 l of a precipitated cobalt catalyst having the following composition:
67% by weight of cobalt, calculated as CoO
19% by weight of copper, calculated as CuO
7% by weight of manganese, calculated as Mn$_3$O$_4$
4% by weight of molybdenum, calculated as MoO$_3$
3% by weight of phosphorus, calculated as H$_3$PO$_4$.

The second catalyst bed closest to the reactor outlet comprised a supported nickel-on-silica catalyst having the following composition:
8% by weight of nickel, calculated as Ni
13% by weight of molybdenum, calculated as MoO$_3$
Balance: SiO$_2$.

After the hydrogenation, the reaction mixture had, according to the gas chromatogram, the following composition in % by area:
Pentanol 45%
TCD-Monoalcohol 5%
TCD-Diol 50%

940 g of this output were distilled in a laboratory apparatus to give 460 g of TCD-diol having an OH number of 550 mg of KOH/g of sample. The OH number, also referred to as hydroxyl number, is the measure which indicates the number of milligrams of potassium hydroxide which are equivalent to the amount of acetic acid bound by 1 g of substance on acetylation. To determine the OH number, the sample is boiled with acetic anhydride/pyridine and the acid formed is titrated with KOH solution (DIN 53240 and DIN 16945). TCD-Diol has a theoretical OH number of 572 mg of KOH/g of sample. The TCD-diol content of the sample is thus (550/572)×100≈96%.

EXAMPLE 5 (According to the Invention)

Reductive Amination of TCD-dialdehyde

TCD-Dialdehyde from the miniplant was reductively aminated over Raney Ni in tetrahydrofuran. For this purpose, 20 g of TCD-dialdehyde (purity: 90%) were reacted in 70 g of THF and 30 g of NH$_3$ over 5 g of Raney Ni at 100° C./200 bar of H$_2$ in an autoclave over a period of 10 hours.

After the end of the experiment, the catalyst was filtered off and the solvent was removed. The residue was analyzed by means of coupled GC-MS: this found the isomeric diamines together with unreacted dialdehyde. The amine number determined on the product mixture which had been freed of solvent was 504 mg of KOH/g (theoretical: 583 mg of KOH/g). For the present purposes, the amine number is the amount of potassium hydroxide in mg which is equivalent to the amine present in 1 g of substance. It is determined by titrating the sample with hydrochloric acid in methanol and converting the hydrochloric acid consumption into KOH equivalents in accordance with DIN 53176. TCD-Diamine has a theoretical amine number of 583 mg of KOH/g of sample. The TCD-diamine content of the sample is thus $(504/583)\times 100 \approx 86\%$.

The invention claimed is:

1. A process for preparing tricyclodecanedialdehyde comprising hydroformylation of dicyclopentadiene with a $CO/H_2$ mixture at elevated temperature and under superatmospheric pressure in the presence of a rhodium catalyst, which has not been modified by means of a ligand and is homogeneously dissolved in the hydroformylation medium, wherein the hydroformylation is carried out at a pressure of from 200 to 350 bar in at least two reaction zones, with a reaction temperature of from 80 to 120° C. in a first reaction zone and a reaction temperature of from 120 to 150° C. in a subsequent reaction zone, with the proviso that the reaction temperature in the subsequent reaction zone is at least 5° C. higher than in the first reaction zone.

2. The process according to claim 1, wherein the hydroformylation is carried out at a concentration of the rhodium catalyst, calculated as Rh, of from 2 to 20 ppm by weight in the hydroformylation medium.

3. The process according to claim 1, wherein the hydroformylation is carried out at a reaction temperature of from 105 to 115° C. in the first reaction zone and at a reaction temperature of from 130 to 140° C. in the subsequent reaction zone.

4. The process according to claim 1, wherein the hydroformylation is carried out in two reaction zones.

5. The process according to claim 1, wherein the reaction temperature in the subsequent reaction zone is at least 15° C. higher than in the first reaction zone.

6. A process for preparing tricyclodecanedimethanol comprising:
hydroformylation of dicyclopentadiene with a $CO/H_2$ mixture at elevated temperature and under superatmospheric pressure in the presence of a rhodium catalyst which has not been modified by means of a ligand and is homogeneously dissolved in the hydroformylation medium to form tricyclodecanedialdehyde, separating the rhodium catalyst from the tricyclodecanedialdehyde, and
hydrogenation of the tricyclodecanedialdehyde with a gas comprising molecular hydrogen at elevated temperature and under superatmospheric pressure over a heterogeneous catalyst, wherein the hydroformylation is carried out at a pressure of from 200 to 350 bar in at least two reaction zones, with a reaction temperature of from 80 to 120° C. in a first reaction zone and a reaction temperature of from 120 to 150° C. in a subsequent reaction zone, with the proviso that the reaction temperature in the subsequent reaction zone is at least 5° C. higher than in the first reaction zone.

7. A process for preparing diaminomethyltricyclodecane by comprising:
hydroformylation of dicyclopentadiene with a $CO/H_2$ mixture under superatmospheric pressure and at elevated temperature in the presence of a rhodium catalyst which has not been modified by means of a ligand and is homogeneously dissolved in the hydroformylation medium, separating the rhodium catalyst from the tricyclodecanedialdehyde and reductive amination of the tricyclodecanedialdehyde at elevated temperature and under superatmospheric pressure over a heterogeneous catalyst in the presence of a gas comprising molecular hydrogen and ammonia, wherein the hydroformylation is carried out at a pressure of from 200 to 350 bar in at least two reaction zones, with a reaction temperature of from 80 to 120° C. in a first reaction zone and a reaction temperature of from 120 to 150° C. in a subsequent reaction zone, with the proviso that the reaction temperature in the subsequent reaction zone is at least 5° C. higher than in the first reaction zone.

8. The process according to claim 6, wherein the hydroformylation is carried out at a concentration of the rhodium catalyst, calculated as Rh, of from 2 to 20 ppm by weight in the hydroformylation medium.

9. The process according to claim 6, wherein the hydroformylation is carried out at a reaction temperature of from 105 to 115° C. in the first reaction zone and at a reaction temperature of from 130 to 140° C. in the subsequent reaction zone.

10. The process according claim 6, wherein the reaction temperature in the subsequent reaction zone is at least 15° C. higher than in the first reaction zone.

11. The process according to claim 7, wherein the hydroformylation is carried out at a concentration of the rhodium catalyst, calculated as Rh, of from 2 to 20 ppm by weight in the hydroformylation medium.

12. The process according to claim 7, wherein the hydroformylation is carried out at a reaction temperature of from 105 to 115° C. in the first reaction zone and at a reaction temperature of from 130 to 140° C. in the subsequent reaction zone.

13. The process according to claim 7, wherein the reaction temperature in the subsequent reaction zone is at least 15° C. higher than in the first reaction zone.

14. The process according to claim 1, wherein the rhodium catalyst is formed under the conditions of the hydroformylation reaction from rhodium(III) salts, rhodium(III) oxide, rhodium(III) sulfide or salts of oxo acids of rhodium.

15. The process according to claim 6, wherein the rhodium catalyst is formed under the conditions of the hydroformylation reaction from rhodium(III) salts, rhodium(III) oxide, rhodium(III) sulfide or salts of oxo acids of rhodium.

16. The process according to claim 7, wherein the rhodium catalyst is formed under the conditions of the hydroformylation reaction from rhodium(III) salts, rhodium(III) oxide, rhodium(III) sulfide or salts of oxo acids of rhodium.

17. The process according to claim 1, wherein the $CO/H_2$ mixture comprise a molar ratio $CO:H_2$ of from 39:61 to 41:59.

18. The process according to claim 6, wherein the $CO/H_2$ mixture comprise a molar ratio $CO:H_2$ of from 39:61 to 41:59.

19. The process according to claim 7, wherein the $CO/H_2$ mixture comprise a molar ratio $CO:H_2$ of from 39:61 to 41:59.

* * * * *